United States Patent [19]

Heeschen

[11] Patent Number: 5,311,283
[45] Date of Patent: May 10, 1994

[54] FIBER OPTIC PROBE AND METHOD FOR DETECTING OPTICALLY ACTIVE MATERIALS

[75] Inventor: William A. Heeschen, Midland, Mich.

[73] Assignee: The Dow Chemical Company, Midland, Mich.

[21] Appl. No.: 755,268

[22] Filed: Sep. 5, 1991

[51] Int. Cl.$^5$ .......................... G01J 4/00; G01N 21/00
[52] U.S. Cl. .................... 356/364; 356/370; 356/436; 250/225
[58] Field of Search ............... 356/364–370, 356/73, 72, 432–436, 440–442, 338, 342, 135; 250/225; 385/12

[56] References Cited

U.S. PATENT DOCUMENTS

| | | | |
|---|---|---|---|
| 3,164,663 | 1/1965 | Gale | 356/436 |
| 3,740,155 | 6/1973 | Keller et al. | 356/246 |
| 3,747,940 | 3/1974 | King | 356/365 |
| 4,573,761 | 3/1986 | McLachlan et al. | 385/12 |
| 4,644,153 | 2/1987 | Ida | 250/225 |
| 4,707,134 | 11/1987 | McLachlan et al. | 356/342 |
| 4,909,588 | 3/1990 | Harner et al. | 385/12 |
| 4,948,255 | 8/1990 | Watanabe | 356/367 |
| 4,988,199 | 1/1991 | Paul | 250/225 |
| 5,038,029 | 8/1991 | Martens et al. | 250/225 |
| 5,044,755 | 9/1991 | Landa et al. | 356/440 |

OTHER PUBLICATIONS

Anal. Chem. 1989 publication, pp. 1238-1243; J. Phys. D: Appl. Phys. 24 (1991) pp. 1861-1868.
Industrial Methods of Analysis 6th Edition, Willard, Merrit, Dean, Settle, pp. 421-427.
Guided Wave, Inc. brochure, Process Monitoring Probes.

Primary Examiner—Richard A. Rosenberger
Assistant Examiner—Hoa Q. Pham
Attorney, Agent, or Firm—John K. McCulloch; Timothy S. Stevens

[57] ABSTRACT

The presence and concentration of an optically active constituent of a fluid medium is determined in-situ by immersing in the fluid medium a probe constructed to pass plane polarized light through the fluid medium in first and second passes so as to induce an optical rotation to the plane of polarization. The light is analyzed after the second pass in a manner to provide a plurality of light components whose individual intensities are affected by the induced optical rotation. A light intensity ratio is determined for the individual light components and compared to light intensity ratios obtained from like fluid media having known concentrations of the optically active constituent therein to permit determination of the concentration of the optically active constituent.

33 Claims, 2 Drawing Sheets

FIBER OPTIC PROBE AND METHOD FOR DETECTING OPTICALLY ACTIVE MATERIALS

FIELD OF THE INVENTION

This invention relates to the determination of the presence and concentration of an optically active constituent in a fluid medium by means of a fiber optic probe immersed in such medium.

BACKGROUND OF THE INVENTION

Production of optically pure materials is increasingly important in the chemical industry, particularly in the production of agricultural and pharmaceutical chemicals. In particular, in many of these chemicals, one optically active isomer provides the desired biological or pharmaceutical activity, while other optical isomers are either inactive or produce an adverse or unwanted biological or chemical effect. In the manufacture of these chemicals, there is a need to isolate one specific isomer as an end product.

Heretofore, two methods have been employed to achieve isomer isolation. One method comprises a stereospecific synthesis where one optically active isomer is made to the exclusion of the others, and the other comprises an optical separation where the various isomers are concurrently made and then physically separated from one another using separation columns. In the case of stereospecific synthesis, in-situ measurement of the optically active constituent provides a technique for monitoring the progress of the reaction. On the other hand, for separation methods, in-situ measurement of optical activity of the effluent from the separation column provides a technique for determining when the appropriate optically active isomer is eluting.

Once the optically pure material is manufactured, it typically is blended at some point in time with other materials, which may or may not be optically active, to provide a desired formulation for end use. In the blending operation, the measurement of optical activity of the blend provides a technique for determining when the specified formulation is obtained.

Manual and automatic polarimeters are available for measuring the concentration of optically active constituents in a fluid medium, for example, as detectors in the liquid chromatographic separation of stereoisomers. These polarimeters operate by illuminating one surface of a liquid containing the steroisomers with polarized light and detecting with a polarized analyzer the emerging light from the opposite surface. In these polarimeters, the polarization axis of the incident light is fixed and known while the polarization axis of the analyzer is variable and also known. Measurement of the optical activity of the liquid requires that a static or dynamic liquid sample be placed into the polarimeter between a polarized light source and the polarized analyzer. The axially spaced light source and analyzer provide a single light path of appropriate length through the liquid sample. The necessity of placing the liquid sample between the light source and the analyzer has limited the application of these polarimeters in the in-situ analysis of optically active constituents in chemical manufacturing and formulation processes.

SUMMARY OF THE INVENTION

The invention relates to a fiber optic probe for detecting the presence of an optically active constituent in a fluid medium while the probe is immersed in the fluid medium. The probe comprises a fluid-tight housing having a chamber for accommodating the medium when the probe is immersed therein. The probe includes light input means in the housing for transmitting incident plane polarized light to the chamber for a first pass through the medium to induce a first optical rotation to the incident light attributable to the optically active constituent of the medium. Reflecting means, such as a mirror, is positioned in the housing in opposing relation to the light input means for reflecting the light back to the chamber for a second pass through the fluid medium.

Suitable means is interposed between the reflecting means and the chamber for altering the first optical rotation before the second pass of the light through the medium in a manner to achieve a second optical rotation during the second pass that, when combined with the first optical rotation, yields a detectable optical effect indicative of the presence and concentration of the optically active constituent. In a preferred embodiment of the invention, the aforementioned light altering means comprises a quarter-wave plate that, in effect, functions as a half-wave plate (by virtue of the light's passing twice therethrough) to reverse the sense of the first optical rotation from positive to negative or vice versa so as to achieve a second optical rotation during the second pass of the light through the fluid medium that is equal and additive to the first optical rotation.

The probe includes light output means positioned in the housing proximate the light input means for collecting the reflected light for analysis in accordance with another aspect of the invention. In particular, the output of the light output means is analyzed to determine the concentration of the optically active constituent in the fluid medium based on changes in the intensity of the polarized light resulting from the first and second optical rotations induced during the first and second passes of the light through the medium. In a preferred embodiment of the invention, the output of the light output means comprises a plurality of individual components of light whose intensity is affected by the optical rotation. The individual intensities are measured and an intensity ratio is calculated and compared to reference intensity ratios obtained from like fluid media having known concentrations of the optically active constituent. The light output means includes a unique arrangement of polarized analyzers for providing the plurality of light components for analysis by a light intensity measuring device and by a computer that calculates and compares light intensity ratios.

In one embodiment the polarizers and analyzers are contained within the body of the probe, whereas in another embodiment the polarizers and analyzers are remote from the probe.

THE DRAWINGS

DETAILED DESCRIPTION OF THE INVENTION

Figure 1:
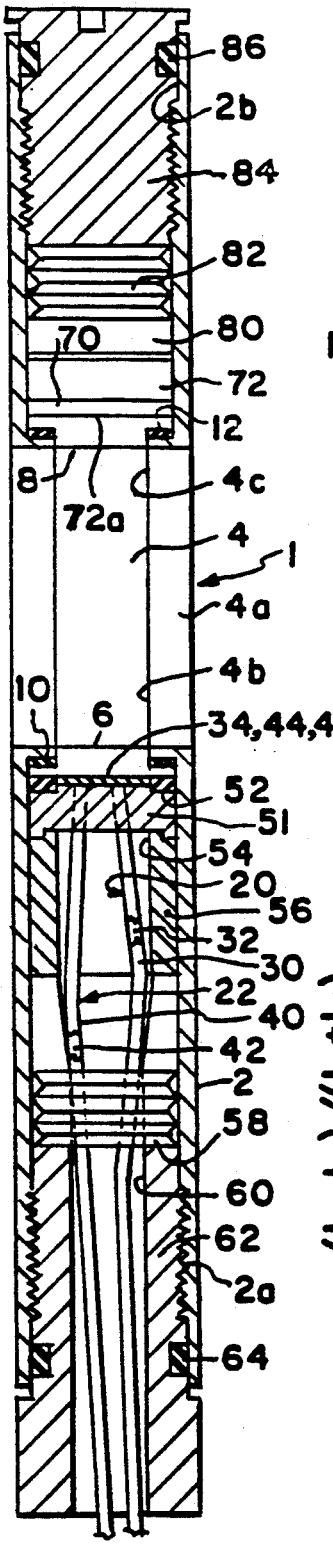
FIG. 1 is a longitudinal sectional view of a fiber optic probe constructed in accordance with one embodiment of the invention.

A fiber optic probe 1 constructed in accordance with one embodiment of the invention is illustrated in FIG. 1 as comprising a hollow, cylindrical, elongate body or housing 2 formed of a suitable metal (e.g., type 316 austenitic stainless steel) or other material capable of immersion without adverse consequences in a fluid medium comprising one or more optically active constituents. The housing 2 includes internally threaded, opposite ends 2a,2b and an elongate chamber 4 therebetween for receiving the fluid medium to be analyzed. The chamber 4 has diametrically opposite, open sides 4a through which the fluid medium can enter and exit the chamber 4 for analysis. As shown in FIG. 1, the chamber 4 includes axial ends 4b,4c that are closed by respective quartz stepped windows 6, 8 sealed to the housing 4 via respective flat, annular gaskets 10,12 to prevent fluid leakage past the windows.

The probe 1 is constructed as a so-called single-ended, fiber-optic probe in that both a light input means 20 and light output means 22 are positioned at the same end 2a (near end) of the housing 2. The light input means 20 comprises first and second clad optical input fibers 30,32 of substantially uniform diameter and an input polarizer member 34 (see FIG. 2). In the embodiment of FIG. 3, the polarizer 34 is within the confines of the probe body. The input fibers 30,32 are connected to a source 33 of monochromatic light of given wavelength by a 50:50 spliced-fiber light splitter 35 (see FIG. 3). A 2 mW HeNe laser operating at a wavelength of $\lambda = 632.8$ nm is useful in practicing the invention with respect to analyzing sugar solutions. Other light sources, however, such as a sodium lamp D-line, also may be used in the analysis of other fluids.

Propagation through the fibers of monochromatic light from the laser scrambles its polarization such that the light reaching the input polarizer member 34 is unpolarized and of equal intensity in each input fiber 30,32. The polarizer member 34 functions to impart plane polarization to the light emerging therefrom toward the chamber 4. A polarizer member 34 useful in practicing the invention exhibits an extinction ratio of approximately 1:1000 such that light polarized parallel to the polarization axis A of the polarizer member is allowed to pass with an intensity 1000 times greater than light polarized perpendicular to the polarization axis A. As shown best in FIG. 2, the polarizer member 34 has a semi-circular profile that permits both of the input fibers 30,32 to be positioned adjacent thereto. Separate polarizer members can be used in lieu of the single polarizer member shown.

Figure 2:
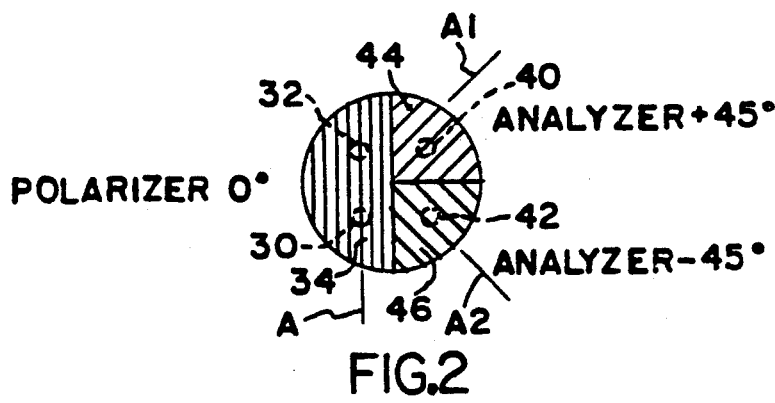
FIG. 2 is an elevational view of the light input polarizer member and the light output polarized analyzer members of the probe of FIG. 1 with the input and output optical fibers shown in phantom behind the polarizer members.
Figure 3:
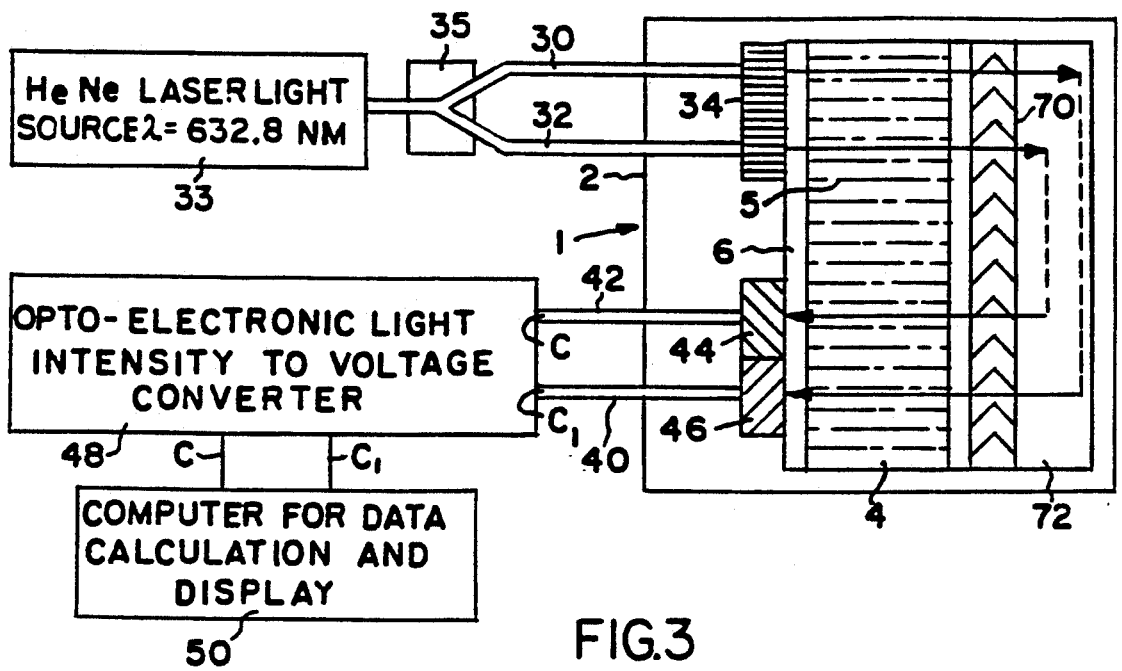
FIG. 3 is a highly schematic view of the probe of the invention illustrating the optical rotation of the plane polarized light during the first and second passes through the fluid medium, and showing the polarizer and analyzers within the confines of the probe body.

The light output means 22 comprises first and second clad optical output fibers 40,42 of substantially uniform diameter and associated output polarized analyzer members 44,46 (see FIG. 2). The output fibers 40,42 are proximate and alongside the light input fibers 30,32 in the housing 2 and connected outside the housing to an opto-electronic light-to-voltage converter 48 (see FIG. 3) and a computer 50. The polarized analyzer members 44,46 of the embodiment shown in FIGS. 1 and 3 are within the confines of the probe body and oriented with their polarization axes A1,A2 angularly displaced from one another. Preferably, the axes A1,A2 are oriented at plus and minus 45° to define a 90° included angle therebetween as shown best in FIG. 2. The axes A1,A2 also are oriented at opposite 45° angles to the polarization axis A of the input polarizer member 34.

The arrangement of the input and output fibers 30,32; 40,42 as shown in FIG. 2 defines an annular pattern with the output fibers 40,42 diametrically disposed relative to the associated input fibers 30,32. The arrangement of the semi-circular input polarizer member 34 and the quarter-circle output polarized analyzer members 44,46 defines a circle that confronts the annular pattern of the input and output fibers.

The input and output fibers 30,32; 40,42 and the associated polarizer and analyzer members 34 and 44,46 are attached to a brass support plug 51 that is sealed to the stepped window 6 by a flat, annular gasket 52. The input and output fibers extend from the plug 51 through a longitudinal bore 54 in an adapter ring 56, through a series of Bellville washers 58, and through a longitudinal bore 60 of a mounting insert 62 threadedly accommodated in the threaded end 2a of the housing 2. The insert 62 is sealed to the housing via an O-ring 64. As is apparent from FIG. 1, threading of the insert 62 into the housing 2 will effect compression of the Bellville washers 58 and establish a bias on the gasket 10 to provide a fluid-tight seal between the chamber 4 and the optical components disposed in the end 2a of the housing.

In practicing the invention, light input and output fibers 30,32; 40,42 comprising 600 micron diameter HCS optical fibers available from Ensign-Bickford Optics Co., P.O. Box 1260, 150 Fisher Dr., Avon, Conn. 06001 successfully have been used. These fibers were mounted in the support plug 51 using high temperature-curing epoxy and then the ends of the fibers were polished with fine polishing paper.

Disposed in the other end 2b (far end) of the housing 2 adjacent the stepped window 8 are a quarter-wave plate 70 (light altering means) and a mirror 72 (light reflecting means) that function in a manner to be described in more detail below. The quarter-wave plate 70 may comprise a single-order wave plate or a multiple-order wave plate available commercially from Melles Griot, 300 East River Road, Rochester, N.Y. 14623. The thickness of the wave plate is selected in dependence upon the wavelength of the incident plane polarized light to provide the desired wave retardation effect. In a preferred embodiment the mounting of the quarter-wave plate 70 is such that its principal axis is parallel to the polarization of the polarizer 34. The mirror 72 comprises a BK7 plate aluminized on the surface 72a that is proximate the quarter-wave plate 70.

In a preferred embodiment the mounting of the quarter-wave plate 70 is such that its principal axis is parallel to the polarization of the polarizer 34.

An adapter plate 80, Bellville washers 82, and an elongate cap 84 also are received in the end 2b of the housing 2. An O-ring 86 seals the cap 84 to the housing 2. As is apparent from FIG. 1, threading of the cap 84 into the housing 2 will effect compression of the Bellville washers 82 and establish a bias on the gasket 12 to provide a fluid-tight seal between the chamber 4 and the optical components located in the end 2b of the housing.

In the construction and assembly of the parts of the probe described above, care should be taken to insure proper parallelism of the optical components involved. In the disclosed probe, focusing optics are omitted from the input and output fibers to simplify probe design. As a result, the input and output fibers 30,32; 40,42 are oriented at a slight angle (e.g., 3.6°) relative to the longitudinal axis of the probe such that extensions of the axes of the input and output fibers intersect at the reflective surface 72a (aluminized surface) of the mirror 72. This maximizes light throughput without focusing. Focusing optics, however, can be included in the design and construction of the optical components in a manner to improve light throughput.

Operation of the probe 1 is schematically illustrated in FIG. 3. wherein split, parallel, randomly-polarized light beams from the light source 33 pass through the polarizer member 34 to impart plane polarization to the light. The plane polarized light then travels in a first pass through the fluid medium 5 occupying the probe chamber 4 and containing one or more optically active constituents. Illustrative of the fluid medium is a solution of one or more steroisomers in a solvent or a mixture of a plurality of steroisomers.

Optical activity refers to the ability of a material to interact differentially with polarized components of electromagnetic radiation, such as the clockwise and anticlockwise circularly polarized light beam components (0° phase displacement) of the incident plane polarized light emerging from the polarizer member 34. One mode of optical activity exhibited by materials comprises circular birefringence which refers to the ability of the optically active material to rotate plane polarized light of a given wavelength relative to the direction of incident polarization. As the two circularly-polarized beams of plane-polarized light pass through the optically-active material, a nonzero phase displacement develops due to the unequal propagation speeds experienced by the two light components and imparts a rotation to the plane of polarization. The sign or sense of the rotation is determined from the perspective of watching the beam of polarized light approach the observer (i.e., approaching analyzer members 44,46) so that clockwise rotations are designated as positive and anticlockwise rotations are designated as negative.

Thus, as a result of travel of the plane polarized light through the fluid medium 5 in the first pass, an optical rotation in one direction (say clockwise) of 10°, for example, is imparted to the plane of polarization.

After the light traverses the fluid medium 5 in the first pass, it passes through the quarter-wave plate 70 and then is reflected by the mirror 72 back through the quarter-wave plate 70 in the direction opposite that of the first pass. As a result of the passage of the light twice through the quarter-wave plate 70, the optical rotation induced during the first pass through the fluid medium is reversed from a positive to a negative sense relative to the analyzer members 44,46 and by an equal amount (e.g., to −10°). In effect, therefore, the quarter-wave plate 70 acts as a half-wave plate by virtue of the light's passing twice therethrough.

The quarter-wave plate thus functions as light-altering means to alter the optical rotation, $\alpha'$, before the light makes a second pass through the fluid medium 5. This change in the optical rotation, $\alpha'$, is selected to achieve a second optical rotation, $\alpha''$, during the second pass of the light through the fluid medium 5 that, when combined with the first optical rotation, yields a detectable optical effect that is indicative of the presence and concentration of a particular optically active constituent of the fluid medium. In the described embodiment the change in optical rotation achieved during the second pass of the light through the fluid medium imparts a second optical rotation that is equal and additive to the first optical rotation. For example, the total detected optical rotation in this embodiment would equal the first optical rotation (after being reversed by passing twice through the quarter-wave plate 70) plus the second optical rotation so as to provide a detectable optical rotation, $\alpha$, of −20° relative to the output polarized analyzer members 44,46.

The reflected light is collected by the light output means 22 (fibers 40,42) described above after the second pass through the fluid medium 5 for analysis in a manner to determine the concentration of the optically-active constituent. In particular, the output polarized analyzer members 44,46 of the light output means 22 select two components C,C$_1$ of the reflected light for transmission to the converter 48 where the intensity of each component can be measured. Since the optical rotation imparted to the collected light affects the intensity of the two components in dependence on the concentration of the optically-active constituent in the fluid medium, measurement of these intensities provides a technique for determining concentration of the optically-active component in the fluid medium 5.

For example, the intensities of the light components C,C$_1$ selected by the orthogonal polarized analyzer members 44,46 can be expressed as follows:

$$I_A = I_0[\cos^2(\theta + 45° - \alpha) + E\cos^2(\theta - 45° - \alpha)]$$

$$I_B = I_0[\cos^2(\theta - 45° - \alpha) + E\cos^2(\theta + 45° - \alpha)]$$

wherein the subscripts A and B refer to the intensity of the two light outputs C,C$_1$ transmitted from the polarized analyzer members 44,46 through output fibers 40,42; $\theta$ is the effective angle between the polarization axis of the polarizer member 34 and the bisector of the orthogonal analyzer members 44,46; and the angles +45° and −45° modify $\theta$ to describe the actual effective angles between the polarization axis A and the axes A1,A2, respectively, as shown in FIG. 2. The term "effective angle" is explained below. The sums and differences of $I_A$ and $I_B$ yield relatively simple expressions for the optical rotation, $\alpha$, as will become apparent below.

With no sample present, if the principal axis of the quarter-wave plate 70 is parallel to the polarization axis A, then the reflected light polarization from the second pass will be parallel to the light from the first pass and the effective angle $\theta$ will be equal to the physical angle $\theta'$ between the polarization axis A of the polarizer member 34 and the bisector of the orthogonal analyzer members 44,46. Again, with no sample present, if the principal axis of the quarter-wave plate 70 is at an angle, $\beta$, relative to the polarization axis A, instead of being parallel thereto, then the reflected light from the second pass will be at the angle $2\beta$ relative to the polarization axis A. Now the effective angle $\theta$ between the polarization axis A of the polarizer member 34 and the bisector of the orthogonal analyzer members 44,46 is equal to the sum of the physical angle $\theta'$ and $2\beta$: $\theta = \theta' + 2\beta$. In the current example, $\theta = 0°$.

If $\alpha$ represents the total optical rotation and $\theta$ represents the effective offset, $\theta' + 2\beta$, of the unrotated polarization due to the physical geometry of the polarizers and analyzers and the angle β between the polarizer axis A and the quarter-wave plate principal axis, then the equations for $I_A$ and $I_B$ can be used directly to describe the intensities of the two light outputs transmitted by output fibers 40,42. Utilizing trigonometric identities in the equations for $I_A$ and $I_B$ and then summarizing and simplifying yields the following equation:

$$\frac{I_A - I_B}{I_A + I_B} = -\sin(2\theta - 2\alpha) \cdot \frac{1-E}{1+E} \quad (II)$$

This equation describes the relationship of optical rotation, α, to the measured intensities of the two light outputs of the light output means 22. The two constants or coefficients, θ and E (overall extinction coefficient for the polarizer/polarized members and the quarter-wave plate), can be determined with calibration samples.

Referring to FIG. 3, the light intensity-to-voltage converter 48 comprises a light-sensitive diode device available from United Detector Technology, 3939 Landmark St., Culver City, Calif. 90230 that provides voltage signals to the computer 50 representative of the measured light intensities of the two light outputs. The computer 50 is a Macintosh SE from Apple Computer, Cupertino, Calif. equipped with a GWI-625 SE data acquisition board from GW Instruments of Cambridge, Mass. and LabVIEW data acquisition software from National Instruments of Austin, Tex. and is programmed to calculate the intensity ratio, $(I_A-I_B)/(I_A+I_B)$, set forth in the above equation (II). The computer also includes a calculational comparator to compare the calculated intensity ratio with stored reference intensity ratios determined by analysis of like fluid media having known concentrations of the optically active constituent therein using the same analysis technique as described above. After these calculating and comparing steps, the computer will display and/or print out the measured concentration of the optically active constituent in the fluid medium analyzed.

Operation of a probe constructed in accordance with the above-described embodiment of the invention was verified with test solutions of known optical activity. Measurements of these test solutions were ultimately used to determine the value of the constants, θ and E, in the above equation (II). The Table set forth below provides the solution compositions, expected optical rotation, and the measured light outputs for the calibration solutions.

TABLE

| Solution Composition | Calculated Optical Rotation, in ° | Signal, $I_A$, in V | Signal, $I_B$ in V | $\frac{I_A - I_B}{I_A + I_B}$ |
|---|---|---|---|---|
| 0.05001 g/mL β-D-(−)-fructose | −1.5 | 2.2000 | 0.6330 | 0.5531 |
| 0.1623 g/mL β-D-(−)-fructose | −4.9 | 2.3761 | 0.5301 | 0.6352 |
| 0.3393 g/mL β-D-(−)-fructose | −10.3 | 2.3289 | 0.3425 | 0.7436 |
| 0.6154 g/mL β-D-(−)-fructose | −18.8 | 3.0423 | 0.2428 | 0.8522 |
| Deionized Water | 0.0 | 1.8398 | 0.6122 | 0.5007 |
| 0.6120 g/mL D-(+)-glucose | +10.8 | 0.7275 | 0.4650 | 0.2201 |

The data set forth in the Table were generated using a light wavelength of λ=632.8 nm from a 2 mW HeNe laser and using a chamber 4 having a length of 1.95 cm. The constants or coefficients, θ and E, were determined by fitting the measured values of $(I_A-I_B)/(I_A+I_B)$ from the Table to the known optical rotations, α, calculated from the solution concentrations. The best fit values were θ=107.7° and E=0.05795 in equation (II).

Figure 5:
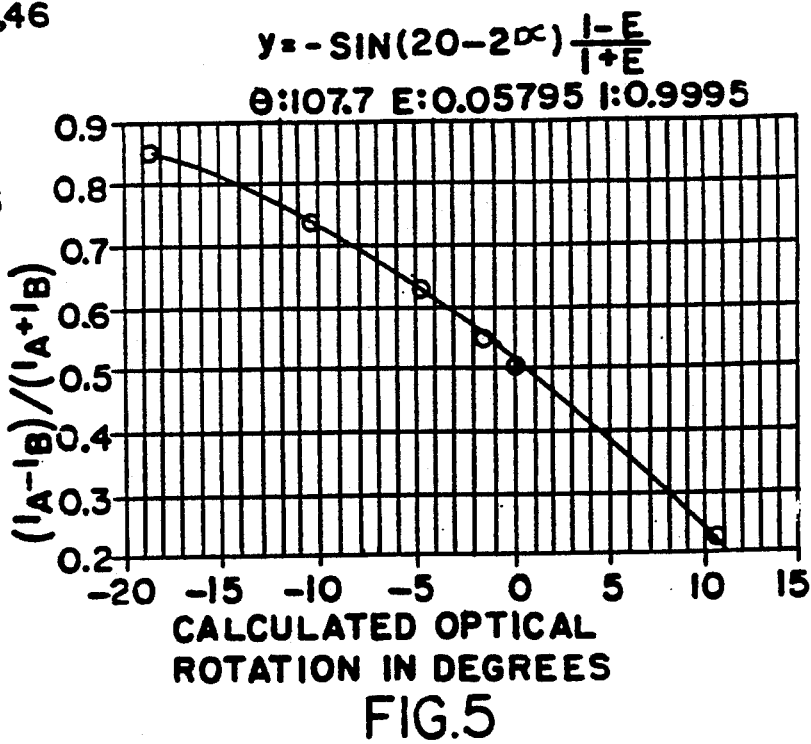
FIG. 5 is a calibration graph of the probe of FIG. 1 obtained using sugar solutions of known optical activity.

The data and plot of the fit equation are shown in FIG. 5. A value of the regression coefficient, r, of 0.9993 indicates a reasonably good fit of the equation set forth above to the data. The probe exhibited a sensitivity to rotations of approximately 1.0°.

Although the invention has been described as using a splitter to provide two light inputs and two light outputs, the invention is not so limited and can be practiced using one light input and one light output. However, the two light output scheme is preferred to provide a broader range of detection of the optical rotation angle, α, and to avoid problems associated with fluctuations in light intensity during the analysis.

The foregoing description of the invention has been confined to the embodiment shown in FIGS. 1 and 3 wherein the polarizer 34 and the analyzers 44 and 46 are within the confines of the probe body 2. It is possible, however, to locate the polarizer and analyzers externally of the probe body by using known optical fibers having polarization preserving properties which are capable of transmitting plane polarized light while preserving the polarization thereof. This characteristic of the invention is shown in FIG. 4 wherein the polarizer 34 and the analyzers 44 and 46 are the same as those described earlier, but are positioned outside the probe body 2 and remote from the latter.

Figure 4:
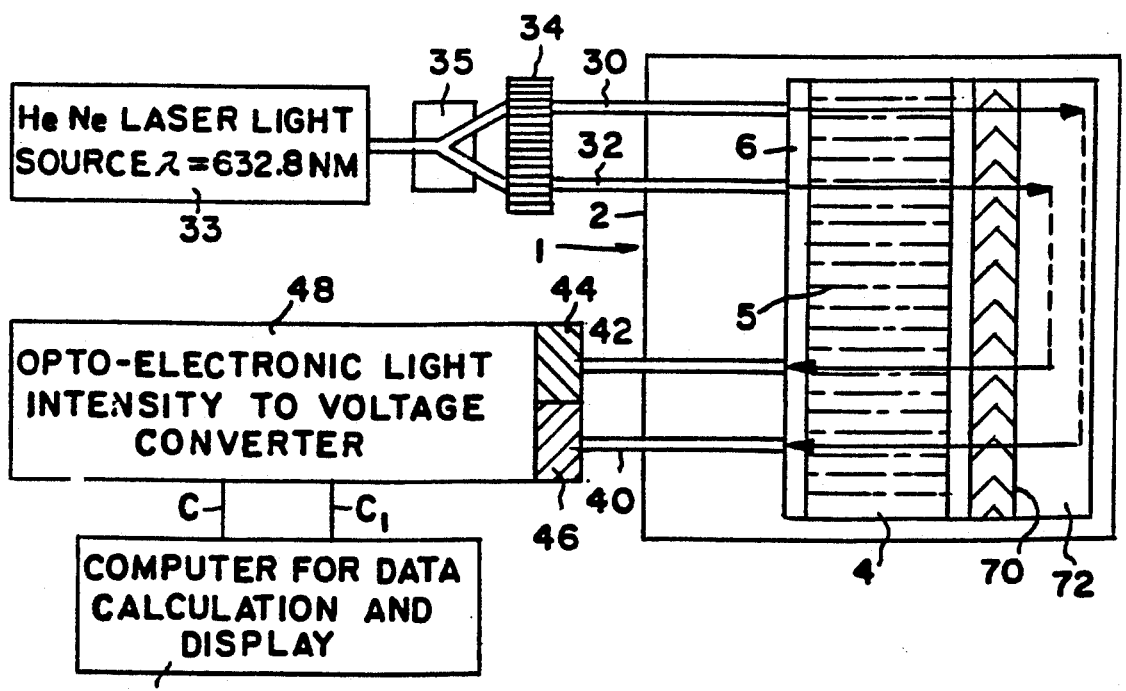
FIG. 4 is a view similar to FIG. 3, but showing the polarizer and analyzers in positions remote from the probe body.

Except for the fact that the optical fibers of the FIG. 4 embodiment are polarization preserving fibers, the embodiments of FIGS. 3 and 4 are the same.

In the embodiment of FIG. 4 the angles of the polarized components of the output light selected by the analyzers relative to each other and to the input polarization will depend on the orientation of the output fibers 40,42 relative to the analyzers 44,46.

If the light source is one which provides stable polarized light and the splitter 35 is one which preserves the polarization, the use of polarization preserving fibers between the splitter and the chamber 4 permits the polarizer to be omitted.

The probe of the invention provides for analytical determination of the presence and concentration of optically active constituents in a fluid medium, without the need to remove samples therefrom. The probe is immersible in the fluid medium, which may be static or dynamic, for direct in-situ analysis. The invention has utility in the measurement of optical activity of fluid media where it is difficult or counterproductive to remove samples for analysis. For example, the invention may be used to monitor stereospecific synthesis and separation. The invention can be used to monitor in-situ reaction kinetics and the extent of reaction as well as formulation processes on both a laboratory and production scale.

I claim:

1. An optical probe for use in determining the presence of an optically active constituent in a fluid medium comprising:

a) a housing having a chamber for accommodating said medium, b) incident light input means for transmitting plane polarized light to said chamber for a first pass through said medium to induce a first optical rotation to the incident light attributable to an optically active constituent of said medium, c) means for reflecting the incident light passed through said chamber back to said chamber for a second pass through said medium, d) a quarter-wave plate interposed between the reflecting means and the chamber in the path of the incident light and the reflected light for altering the first optical rotation before said second pass through said medium to achieve a second optical rotation during said second pass that is attributable to said optically active constituent and, when combined with the first optical rotation, yields a detectable optical effect, and e) light output means for collecting the reflected light.

2. The probe of claim 1 wherein the incident light input means comprises at least one optical fiber.

3. The probe of claim 1 wherein said plane polarized light is emitted from a polarizing source thereof.

4. The probe of claim 1 including polarizing means between said chamber and a source of light for polarizing said light.

5. The probe of claim 4 wherein said polarizing means is positioned within the confines of said housing.

6. The probe of claim 4 wherein said polarizing means is external of said housing.

7. The probe of claim 1 wherein said quarter-wave plate reverses said first optical rotation such that the second optical rotation is additive to the first optical rotation.

8. The probe of claim 1 wherein the light output means comprises at least one optical fiber and a polarized analyzer between the fiber and the chamber.

9. The probe of claim 8 wherein said analyzer is within the confines of said housing.

10. The probe of claim 8 wherein said analyzer is external of said housing.

11. The probe of claim 1 wherein the housing chamber comprises an elongated, open-sided cavity through which the medium flows.

12. An apparatus for determining the concentration of an optically active constituent in a fluid medium comprising the optical probe of claim 1 wherein the light output means provides a light output whose intensity is affected by the optical rotation induced during the first and second pass through the fluid medium, said apparatus further comprising means coupled to the light output means of said probe for measuring the intensity of the light output, and means for comparing the measured intensity with a reference intensity obtained from a like fluid medium having a known concentration of the optically active constituent therein.

13. The apparatus of claim 12 wherein the light output means provides a light output having a plurality of components whose intensities are affected by the optical rotation induced during the first and second passes through the fluid medium.

14. The apparatus of claim 13 wherein said light intensity measuring means measures the intensity of the individual polarized components of the light.

15. The apparatus of claim 14 including means for calculating an intensity ratio using the measured intensities of said components for comparison by said comparing means to a reference intensity ratio determined from said like fluid medium.

16. An optical probe for use in determining the presence of an optically active constituent in a fluid medium, comprising:

a) a fluid tight housing immersible in the fluid medium, said housing having a chamber therein for receiving said medium, b) light input means for transmitting incident planar polarized light along a path from a source thereof to one end of said chamber for a first pass through said medium to impart a first optical rotation to the incident light attributable to the optically active constituent of said medium, c) reflective means in the path of said light at the opposite end of said chamber for reflecting the incident light back along a reverse path to said chamber for a second pass through said medium, d) means plate between the reflective means and the chamber and in the path of the light for altering the first optical rotation before said second pass through said medium so as to achieve a second optical rotation during said second pass that is attributable to said optically active constituent and is additive to said first optical rotation, and e) light collecting means for collecting the reflected light.

17. The probe of claim 16 wherein the light input means comprises first and second optical input fibers for transmitting said light and input polarizer means between the input fibers and the chamber for imparting plane polarization to the light passing through the chamber.

18. The probe of claim 17 wherein the light collecting means comprises first and second optical output fibers oriented to collect light reflected from the respective first and second optical input fibers, and respective first and second output polarized analyzer members between each respective output fiber and the chamber.

19. The probe of claim 18 wherein the polarized analyzer members have polarization axes angularly displaced from one another.

20. The probe of claim 19 wherein the polarization axes define a 90° angle therebetween.

21. An apparatus for determining the concentration of an optically active constituent in a fluid medium comprising the optical probe of claim 16 wherein the light collecting means provides a light output whose intensity is affected by the optical rotation induced during the first and second passes through the fluid medium, said apparatus further comprising means coupled to the light collecting means for measuring the intensity of the collected light, and means for comparing the measured intensity with a reference intensity obtained from a like fluid medium having a known concentration of the optically active constituent therein.

22. An optical probe as defined in claim 16 further characterized in that said means for altering the first optical rotation comprises a quarter-wave plate whereby the light passes through said plate once before reflection from the reflective means and once after the light has been reflected.

23. An optical probe as defined in claim 16 further characterized by:

said means between the reflective means and the chamber providing a retardation of one component of said light one-half wave length with respect to a perpendicular component of said light for changing the plane of the planar polarized light after said first pass through said medium but before said second pass.

24. A method of determining the presence of an optically active constituent in a fluid medium comprising the steps of:
  a) directing plane polarized light in a first pass through the fluid medium in a first direction to induce a first optical rotation of the plane of polarization attributable to the optically active constituent,
  b) altering the first optical rotation of the light following said first pass through said fluid medium by retarding one component of said light one-half wave with respect to a perpendicular component of said light,
  c) reflecting the light following said first pass for a second pass through said medium, said second pass following the altering of the first optical rotation to achieve a second optical rotation during the second pass attributable to the optically active constituent and combinable with the first optical rotation to yield a detectable optical effect, and
  d) collecting the light from the second pass for analysis.

25. The method of claim 24 wherein the first optical rotation is altered by passing the light through a quarter-wave plate after the first pass through said medium and again before the second pass through said medium so that the second optical rotation is equal and additive to the first optical rotation.

26. The method of claim 24 including, following step c, analyzing the collected light to determine a present concentration of the optically active constituent.

27. The method of claim 26 wherein the concentration of said constituent is determined by measuring its intensity and comparing the measured intensity with a reference intensity obtained from a like fluid medium having a known concentration of the optically active constituent therein.

28. The method of claim 26 including selecting from the collected light a plurality of individual polarized light components whose intensities are affected by the optical rotation induced during the first and second passes through the fluid medium and measuring the intensity of said individual components.

29. The method of claim 28 including calculating an intensity ratio using the measured intensities of said components and comparing the calculated intensity ratio to a reference intensity ratio determined from a like fluid medium.

30. The method of claim 24 wherein the fluid medium contains stereoisomers.

31. In an optical probe for use in determining the presence of an optically active constituent that produces circular birefringence, in a fluid medium, the combination of a source of light; first and second optical input fibers for transmitting light from said source through said fluid medium for a first pass; means for imparting plane polarization to the light transmitted by said fibers before passing through said fluid; a wave retardation device to retard one component of said light one half wavelength with respect to a perpendicular component of said light after said first pass but before a second pass; a reflector for reflecting said light after said first pass to direct said light through said fluid for said second pass; first and second optical output fibers oriented relative to the respective first and second light input fibers to receive therefrom light that traverses said fluid medium after said second pass and transmit such light along a path; and first and second polarized analyzer members for selecting for analysis respective first and second polarized light components from the light received by said output fibers.

32. The combination of claim 31 wherein the first and second polarized analyzer members have polarization axes angularly oriented to one another and to the polarization axis of the input polarizer member.

33. The combination of claim 32 wherein the polarization axes define a 90° angle therebetween.

* * * * *

UNITED STATES PATENT AND TRADEMARK OFFICE
CERTIFICATE OF CORRECTION

PATENT NO. : 5,311,283

DATED : May 10, 1994

INVENTOR(S) : William A. Heeschen

It is certified that error appears in the above-identified patent and that said Letters Patent is hereby corrected as shown below:

Column 10, line 17, "d) means plate between the reflective means and the", should correctly read --d) means between the reflective means and the--.

Signed and Sealed this

Fourth Day of April, 1995

*Attest:*

BRUCE LEHMAN

*Attesting Officer*   *Commissioner of Patents and Trademarks*